US008529497B2

(12) United States Patent
Kim

(10) Patent No.: US 8,529,497 B2
(45) Date of Patent: Sep. 10, 2013

(54) APPARATUS AND METHOD FOR CONTROLLING FECAL DIVERTING DEVICE

(76) Inventor: Jae-Hwang Kim, Daegu (KR)

(*) Notice: Subject to any disclaimer, the term of this patent is extended or adjusted under 35 U.S.C. 154(b) by 858 days.

(21) Appl. No.: 11/950,187

(22) Filed: Dec. 4, 2007

(65) Prior Publication Data

US 2009/0143722 A1 Jun. 4, 2009

(51) Int. Cl.
*A61M 1/00* (2006.01)

(52) U.S. Cl.
USPC ........... 604/31; 604/99.01; 604/276; 604/278

(58) Field of Classification Search
USPC ............. 604/27, 31, 65, 66, 67, 96.01–97.02, 604/99.01, 101.01, 101.05, 102.01–102.03, 604/118, 257, 258, 275, 277, 278, 332, 334, 604/503, 505, 514, 518, 901, 911, 97.03–98.02, 604/101.02, 276, 279; 600/29–32; 606/197
See application file for complete search history.

(56) References Cited

U.S. PATENT DOCUMENTS

| 4,689,041 A * | 8/1987 | Corday et al. ................ 604/509 |
| 6,251,093 B1 * | 6/2001 | Valley et al. ............... 604/97.03 |
| 2003/0195481 A1 * | 10/2003 | Xu et al. ....................... 604/275 |
| 2003/0208156 A1 * | 11/2003 | Pham et al. .................... 604/113 |
| 2004/0039348 A1 * | 2/2004 | Kim et al. ..................... 604/264 |
| 2005/0033226 A1 * | 2/2005 | Kim ......................... 604/101.01 |
| 2007/0197963 A1 * | 8/2007 | Griffiths et al. ............ 604/97.01 |

* cited by examiner

*Primary Examiner* — Kami A Bosworth
(74) *Attorney, Agent, or Firm* — Birch, Stewart, Kolasch & Birch, LLP

(57) ABSTRACT

A fecal diverting device includes an internal balloon formed at the inside of a tubular body part disposed at the front end of a connection tube, at least one external balloon formed at the outside of the tubular body part, and an enema liquid injection hole formed through the forefront of the tubular body part and the at least one external balloon and an enema liquid to be injected into an intestinal tract of a patient via an enema liquid injection hole through a control tube. A device controller connected to the control tube regulates the amounts of fillers filling the internal balloon and the at least one external balloon and controlling the injection of the enema liquid, supplied from an enema liquid supplying unit, into the intestinal tract.

7 Claims, 7 Drawing Sheets

APPARATUS AND METHOD FOR CONTROLLING FECAL DIVERTING DEVICE

BACKGROUND OF THE INVENTION

1. Field of the Invention

The present invention relates to a fecal diverting device, and more particularly to an apparatus and method for controlling a fecal diverting device, which automatically achieves fecal diversion including fecal discharge.

2. Description of the Related Art

Generally, patients, which have a difficulty in voluntarily defecating due to an operation or a long-time treatment, require a fecal discharging treatment using medical appliances inserted into the rectum through the anus. That is, according to circumstances, the above medical appliances suppress fecal discharge, or accelerate fecal discharge using an enema liquid injected into the rectum.

One of fecal discharging technique is disclosed in U.S. Pat. No. 5,569,216 entitled "Multipurpose colostomy device having balloons on an end thereof", which was filed by the inventor of the present invention, i.e., Kim Jae-Hwang, and was registered in 1996.

The above U.S. Pat. No. 5,569,216 discloses the multipurpose colostomy device, which includes an internal balloon, a ring configured external balloon, a connecting tube, a washing fluid passage, etc. This multipurpose colostomy device facilitates fecal discharge, and allows a medicine to be injected into the rectum or the large intestine of a patient.

However, the conventional technique including the above multipurpose colostomy device is disadvantageous in that fecal diversion is carried out manually.

SUMMARY OF THE INVENTION

Therefore, the present invention has been made in view of the above problems, and it is an object of the present invention to provide an apparatus and method for controlling a fecal diverting device, which automatically achieves fecal diversion including fecal discharge.

In accordance with one aspect of the present invention, the above and other objects can be accomplished by the provision of an apparatus for controlling a fecal diverting device, comprising the fecal diverting device provided with an internal balloon formed at the inside of a tubular body part disposed at the front end of a connection tube, at least one external balloon formed at the outside of the tubular body part, and an enema liquid injection hole formed through the forefront of the tubular body part, so as to allow fillers to be respectively injected into the internal balloon and the at least one external balloon and an enema liquid to be injected into an intestinal tract of a patient via an enema liquid injection hole through a control tube; and a device controller connected to the control tube for regulating the amounts of the fillers filling the internal balloon and the at least one external balloon through the control tube based on a predetermined fecal diverting program, and controlling the injection of the enema liquid, supplied from an enema liquid supplying unit, into the intestinal tract via the enema liquid injection hole through the control tube.

In accordance with another aspect of the present invention, there is provided a method for controlling a fecal diverting device, which is provided with an internal balloon formed at the inside of a tubular body part formed at the front end of a connection tube, at least one external balloon formed at the outside of the tubular body part, and an enema liquid injection hole formed through the forefront of the tubular body part, so as to allow fillers to be respectively injected into the internal balloon and the at least one external balloon and an enema liquid to be injected into an intestinal tract of a patient via the enema liquid injection hole through control tube, using a device controller installed at the outside of the anus of the patient through the control tube, comprising filling the internal balloon and the at least one external balloon fully with fillers through the control tube under the condition that the tubular body part of the fecal diverting device is inserted into the intestinal tract through the anus, and injecting the enema liquid into the intestinal tract through the enema liquid injection hole at a predetermined injection speed; sensing an intestinal pressure using an intestinal pressure sensing unit of the device controller connected to the fecal diverting device inserted into the intestinal tract through the control tube; stopping the injection of the enema liquid, when the sensed intestinal pressure reaches a predetermined reference intestinal pressure value; contracting the internal balloon through the control tube, when the sensed intestinal pressure is larger than a predetermined critical intestinal pressure, so as to open the connection tube; and expanding the internal balloon through the control tube, when the sensed intestinal pressure is smaller than the reference intestinal pressure value under the opened state of the connection tube, so as to close the opened connection tube, and injecting the remainder of the enema liquid into the intestinal tract.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Now, preferred embodiments of the present invention will be described in detail with reference to the annexed drawings.

Figure 1:
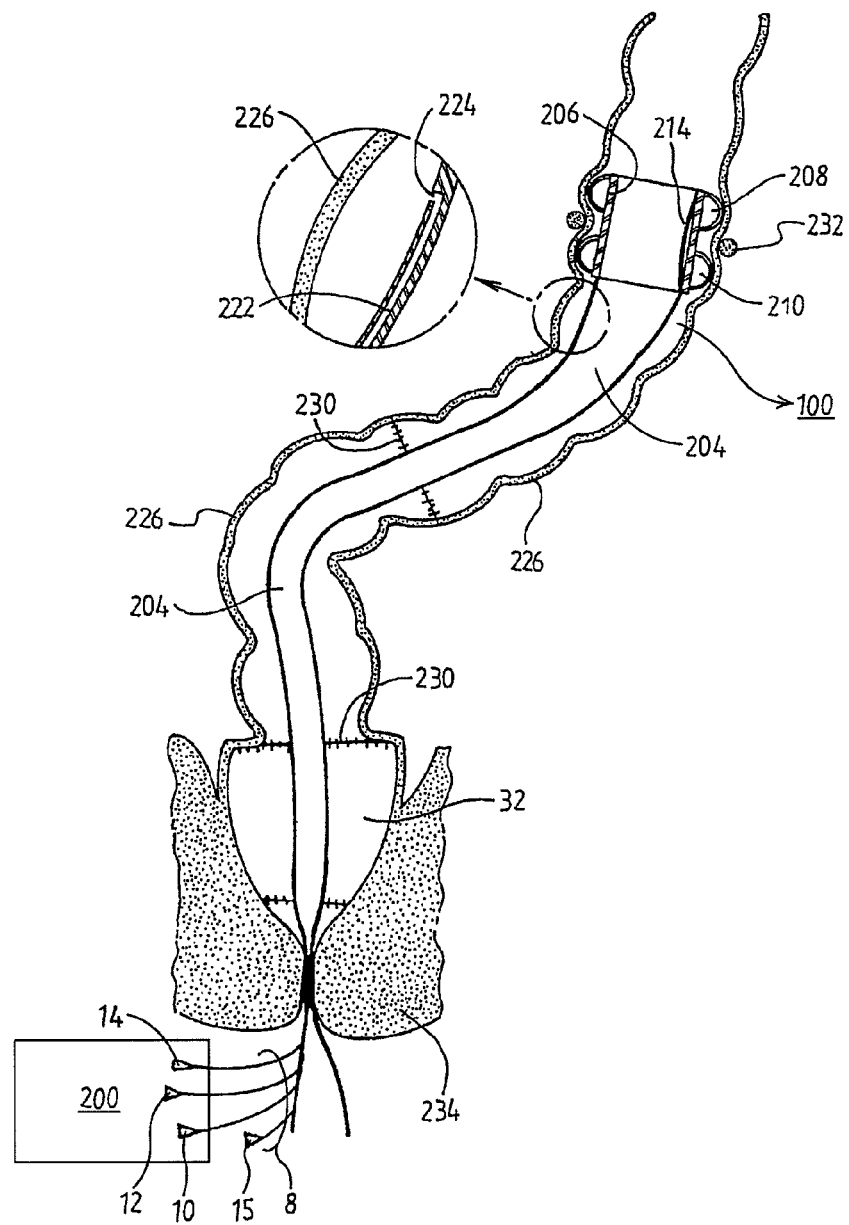
FIGS. 1 and 2 are cross-sectional views illustrating a state in which an apparatus for controlling a fecal diverting device in accordance with an embodiment of the present invention is used.
Figure 2:
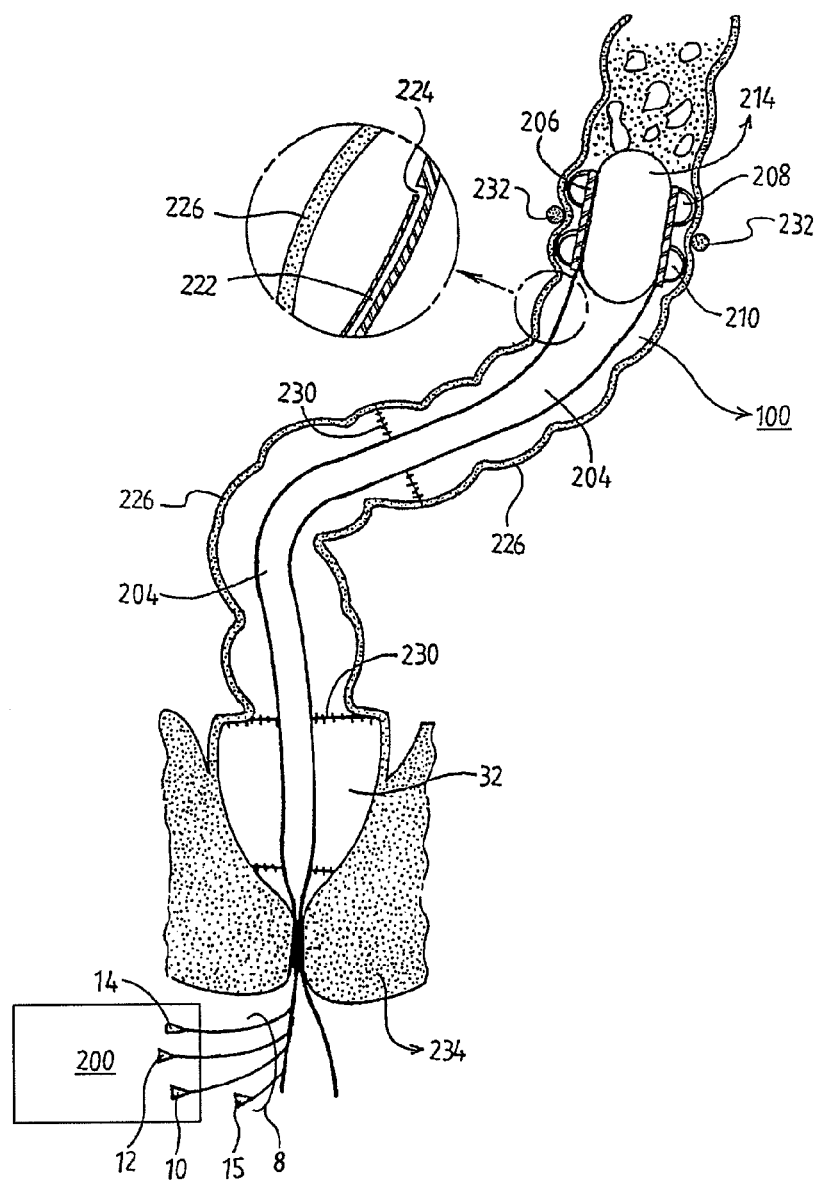

FIGS. 1 and 2 are cross-sectional views illustrating a state in which an apparatus for controlling a fecal diverting device in accordance with an embodiment of the present invention is used. The apparatus includes a fecal diverting device 100, and a device controller 200 for controlling the fecal diverting device 100.

As shown in FIGS. 1 and 2, the fecal diverting device 100, in the case that there is danger of leakage of liquid and gas at an anastomosed portion 230 of a large intestine 226 or a rectum 32 after a patient has undergone an operation on the large intestine or the rectum in the anus, is installed above the anastomosed portion 230 and thus allows feces to be discharged without contact with the anastomosed portion 230.

FIG. 1 illustrates a state in which the fecal diverting device 100 is installed above the anastomosed portion 230 after the operation on the large intestine or the rectum, and is connected to the device controller 200 located at the outside of the anus 234. FIG. 2 illustrates a state in which a tube opening and closing internal balloon 214 is expanded and thus closes the intestinal tract so that intestinal feces are not discharged to the outside of the anus under the state of FIG. 1. Further, FIG. 3 is an enlarged cross-sectional view of a front end portion of the fecal diverting device 100 of FIGS. 1 and 2.

Figure 3:
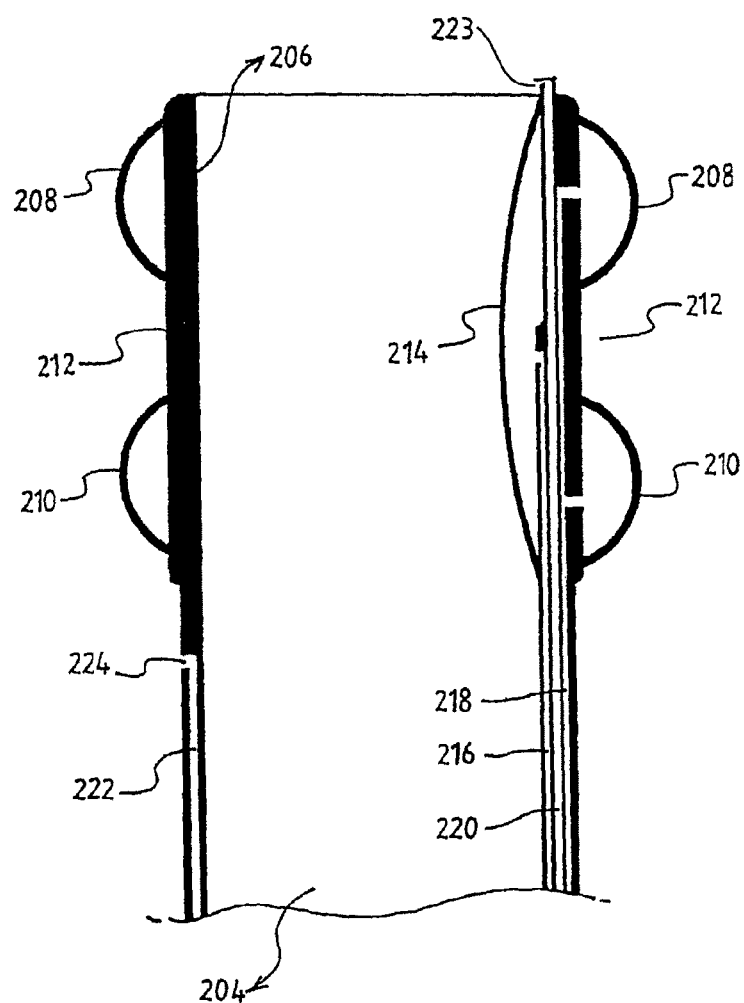
FIG. 3 is an enlarged cross-sectional view of a tubular body part formed at the front end of the fecal diverting device of FIGS. 1 and 2.

In FIGS. 1 to 3, reference numeral "204" is a connection tube, reference numeral "206" is a tubular body part, reference numerals "208, 210" are fixing external balloons, and reference numeral "214" is a tube opening and closing internal balloon. Further, reference numeral "216" is an injection passage for the internal balloon, reference numeral "218" is an injection passage for the external balloons, reference numeral "220" is an enema liquid injection passage, reference numeral "222" is a remedial liquid injection passage for a remedial liquid, and reference numeral "224" is a remedial liquid injection hole. Reference numeral "232" is a clamping band.

An enema liquid injection hole 223 formed through the enema liquid injection passage 220 is opened to the forefront of the tubular body part 206 between the internal balloon 214 and the external balloons 208 and 210 respectively formed at the inside and the outside of the tubular body part 206 located at the front end of the connection tube 204, and the remedial liquid injection hole 224 formed through the remedial liquid injection passage 222 is opened to the outside of the connection tube 204 in the rear of the internal balloon 214 and the external balloons 208 and 210. Fillers respectively filling the internal balloon 214 and the external balloons 208 and 210 may be a filling liquid or a gas, such as air.

The fecal diverting device 100 allows an enema liquid or a washing liquid to be injected thereinto through the enema liquid injection passage 220 and the enema liquid injection hole 223, thus being capable of diluting feces or washing the inside of the connection tube 204. Further, the fecal diverting device 100 allows a remedial liquid, such as an antibiotic, to be injected thereinto through the remedial liquid injection passage 222 and the remedial liquid injection hole 224 and then to be discharged to the outside of the connection tube 204, thereby being capable of sterilizing or treating the anastomosed portion 230 of the large intestine 226 or the rectum 32.

A flexible control tube 8 having respective corresponding passages is extended, together with the connection tube 204, to the internal balloon 214 and the external balloons 208 and 210 of the tubular body part 206, the enema liquid injection hole 223, and the remedial liquid injection hole 224. An internal balloon connector 10, an external balloon connector 12, an enema liquid connector 14, and a remedial liquid connector 15 corresponding to the respective passages are respectively formed on the external end of the control tube 8.

Switch valves BV1 and BV2 (of FIG. 5) are respectively installed in the internal balloon connector 10 and the external balloon connector 12, and a check valve CBV (of FIG. 5) is installed in each of the enema liquid connector 14 and the remedial liquid connector 15. Thereby, when an injector or a correspondent connector of the device controller 200 is inserted into one of the connectors, the correspondent valve is opened, and when the injector or the correspondent connector of the device controller 200 is separated from one of the connectors, the correspondent valve is closed.

Through the control tube 8, fillers are respectively injected into the internal balloon 214 and the external balloons 208 and 210, and an enema liquid and a remedial liquid are respectively injected into the enema liquid injection hole 223 and the remedial liquid injection hole 224.

In the embodiment of the present invention, the fecal diverting device 100, which is installed as shown in FIGS. 1 and 2, controls fecal diversion based on a predetermined fecal diverting program using the external device controller 200, thus automatically performing the fecal diversion. Through the automatic fecal diversion, intestinal feces are discharged to the outside of the anus through the connection tube 204 of the fecal diverting device 100 and are collected in an external collection pack 9 (of FIG. 5).

Figure 4:
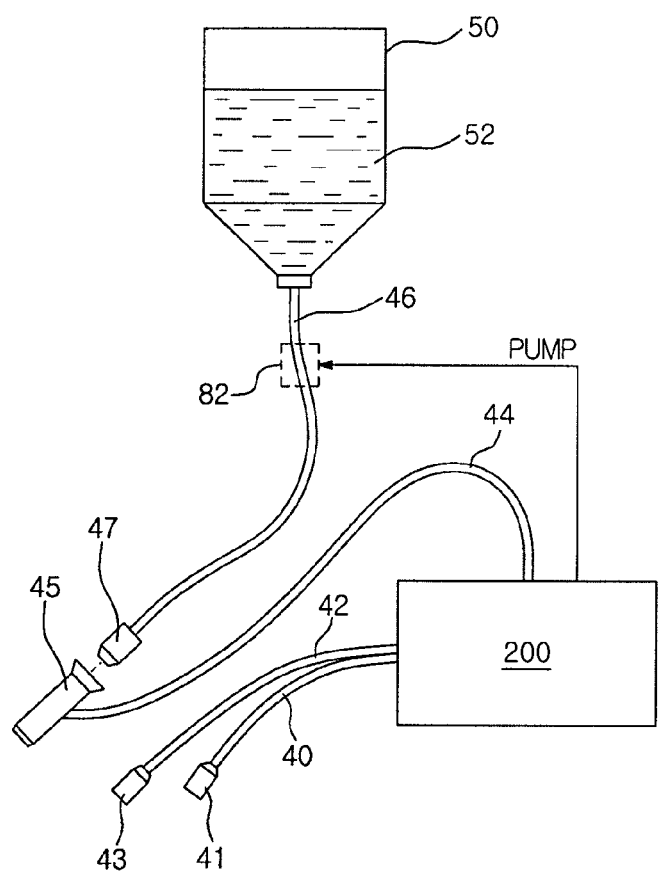
FIG. 4 is a schematic view of a device controller of the apparatus in accordance with the embodiment of the present invention.
Figure 5:
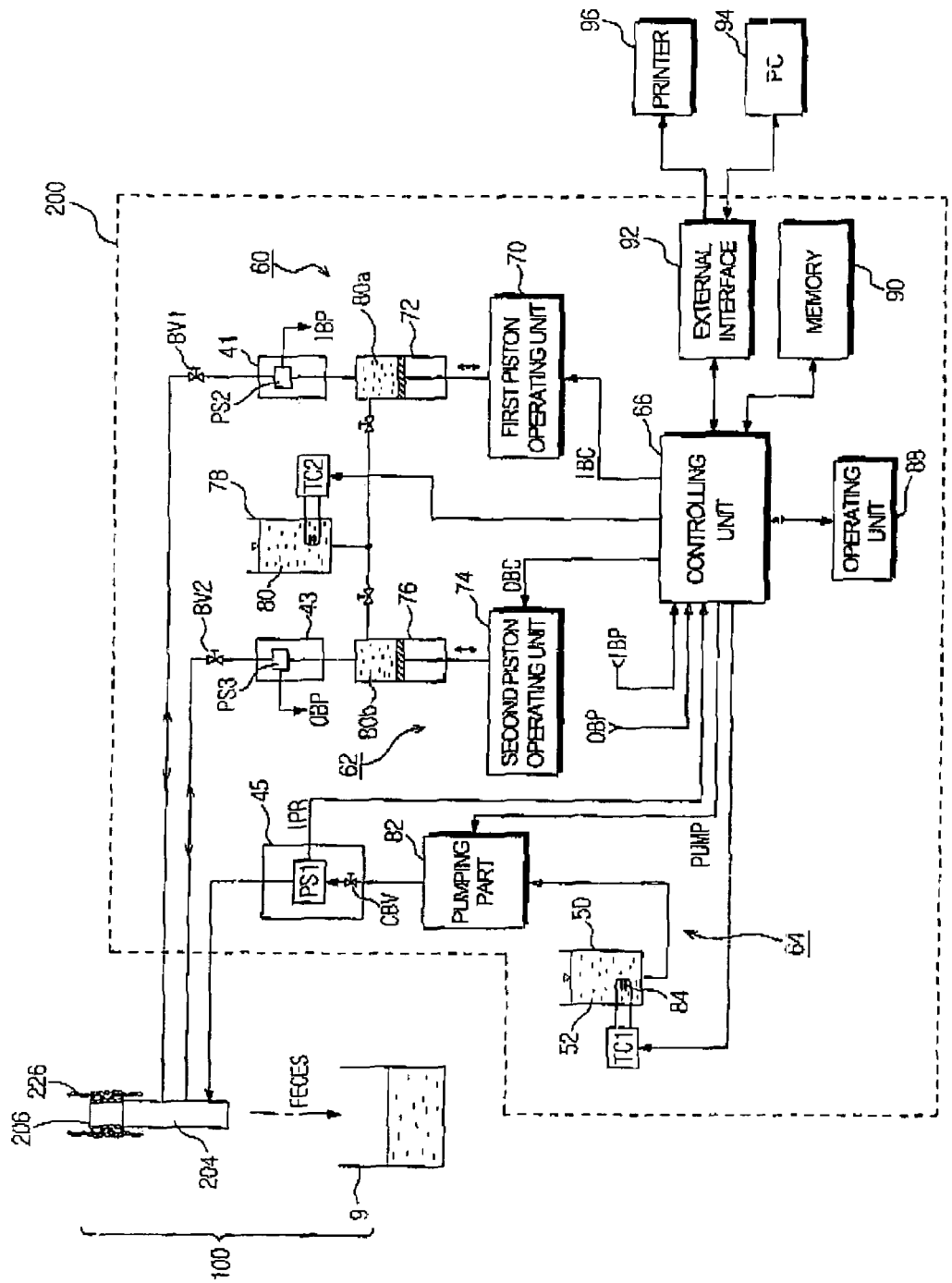
FIG. 5 is a block diagram of the device controller of the apparatus in accordance with the embodiment of the present invention.

FIG. 4 is a schematic view of the device controller 200 of the apparatus in accordance with the embodiment of the present invention, and FIG. 5 is a block diagram of the device controller 200 of the apparatus in accordance with the embodiment of the present invention.

As shown in FIGS. 4 and 5, the device controller 200 of the apparatus in accordance with the embodiment of the present invention is connected to the control tube 8 of the fecal diverting device 100, and controls the amounts of the fillers filing the internal balloon 214 and the external balloons 208 and 210 of the fecal diverting device 100 through the control tube 8 based on the predetermined fecal diverting program and the injection of an enema liquid 52, supplied from an enema liquid supply tub 50 of an enema liquid supplying unit 64 (of FIG. 5), to the enema liquid injection hole 223 of the fecal diverting device 100 through the control tube 8.

In the device controller 200 of FIG. 4, reference numeral "46" is an enema liquid supply tube, and reference numeral "47' is a connector of the enema liquid supply tube 46. Reference numeral "40" is an internal balloon injection tube, and reference numeral "41" is a connector of the internal balloon injection tube 40. Reference numeral "42" is an external balloon injection tube, and reference numeral "43" is a connector of the external balloon injection tube 42. Reference numeral "44" is an intestinal pressure sensing tube, and reference numeral "45" is a socket for connecting the connector 47 of the enema liquid supply tube 46 and the enema liquid connector 14 of the control tube 8.

A check valve CBV (of FIG. 5) for allowing the enema liquid 52 to flow only in one direction from the enema liquid supply tub 50 to the control tube 8 of the fecal diverting device 100 and a pressure sensor PS1 (of FIG. 5) for sensing the intestinal pressure in the upper portion of the intestinal tract, in which the fecal diverting device 100 is installed, are installed in the socket 45. Here, the pressure sensor PSI may be a mechanical sensor or an electronic sensor.

The enema liquid supply tub 50 of FIG. 4 is mounted on a main body of the device controller 200.

As shown in FIG. 5, the device controller 200 includes an internal balloon filling unit 60, an external balloon filling unit 62, the enema liquid supplying unit 64, an intestinal pressure sensing unit (PS1, PS2, and PS3), and a controlling unit 66.

The internal balloon filling unit 60 causes a filler 80a to fill the internal balloon 214 of the fecal diverting device 100 or to be discharged from the internal balloon 214 under the control of the controlling unit 66, and the external balloon filling unit 62 causes a filler 80b to fill the external balloons 208 and 210 of the fecal diverting device 100 or to be discharged from the external balloons 208 and 210 under the control of the controlling unit 66.

As shown in FIG. 5, the internal balloon filling unit 60 includes a first piston operating part 70 and a first piston pump 72, and the external balloon filling unit 62 includes a second piston operating unit 74 and a second piston pump 76. The first piston pump 72 and the second piston pump 76 respectively receive the fillers 80a and 80b from a filler supply tub 78. In the same manner as the enema liquid supply tub 50, the filler supply tub 78 is mounted on the main body of the device controller 200.

The enema liquid supplying unit 64 causes the enema liquid 52 of the enema liquid supply tub 50 to be injected into the intestinal tract above the tubular body part 206 through the enema liquid injection hole 223 of the fecal diverting device 100 under the control of the controlling unit 66. As shown in FIG. 5, the enema liquid supplying unit 64 includes the enema liquid supply tub 50 and a pumping part 82.

The pumping part 82 pumps the enema liquid 52 supplied from the enema liquid supply tub 50 so as to be injected into the intestinal tract through the enema liquid injection hole 223 at a predetermined supply pressure, for example, a pressure of approximately 80 cm $H_2O$. Thus, the pumping part 82 may be omitted, if the enema liquid supply tub 50 is located at a position where the enema liquid supply tub 50 can inject the enema liquid 52 into the intestinal tract through the enema liquid injection hole 223.

The pressure sensor PS1 of FIG. 5 for sensing the intestinal pressure is installed in the socket 45 of FIG. 4 for connecting the connector 47 of the enema liquid supply tube 46 and the enema liquid connector 14 (of FIG. 1) of the control tube 8 of the fecal diverting device 100. The pressure sensor PS1 serves as an intestinal pressure sensing part for sensing the intestinal pressure under the condition that the front tubular body part 206 of the connection tube 204 of the fecal diverting device 100 is inserted into the large intestine 226, and the intestinal pressure sensed by the pressure sensor PS1 is applied to the controlling unit 66 through an intestinal pressure signal IPR.

The controlling unit 66 respectively controls the first piston operating part 70 of the internal balloon filling unit 60, the second piston operating part 74 of the external balloon filling unit 62, and the pumping part 82 of the enema liquid supplying unit 64, based on the fecal diverting program stored in a memory 90 in accordance with the embodiment of the present invention, through the input of the intestinal pressure signal IPR sensed by the pressure sensor PS1. Further, the controlling unit 66 forms a user's interface with an operating unit 88, and communicates with an external controlling device, for example, a PC 94 or a printer 96, through an external interface 92.

The device controller 200 in accordance with the embodiment of the present invention further includes a first temperature regulating unit for regulating the temperature of the enema liquid 52 under the control of the controlling unit 66, and a second temperature regulating unit for regulating the temperature of the fillers 80a and 80b filling the internal balloon 214 and the external balloons 208 and 210 under the control of the controlling unit 66.

In FIG. 5, a temperature controller TC1 and a heater 84 correspond to the first temperature regulating unit, and a temperature controller TC2 and a heater 86 correspond to the second temperature regulating unit. The temperature controllers TC1 and TC2 respectively control the correspondent heaters 84 and 86 such that the heaters 84 and 86 heat the temperature of the enema liquid 52 stored in the enema liquid supply tub 84 and the fillers 80a and 80b in a liquid state stored in the filler supply tub 78 to a temperature similar to the temperature of the human body, for example, 37.5° C.

The first and second temperature regulating units are unnecessary when the main body of the device controller 200 is located in the warm indoor room or in the summer time, and thus are optionally installed by user's selection.

In FIG. 5, a non-described reference mark "PS2" is a pressure sensor, which is selectively installed on the connector 41 of the device controller 200 or the connector 10 of the fecal diverting device 100, senses the filling pressure of the internal balloon 214, and provides an internal balloon filling pressure sensing signal IBP to the controlling unit 66. Further, a non-described reference mark "PS3" is a pressure sensor, which is selectively installed on the connector 43 of the device controller 200 or the connector 12 of the fecal diverting device 100, senses the filling pressure of the external balloons 208 and 210, and provides an external balloon filling pressure sensing signal OBP to the controlling unit 66. The second and third pressure sensors PS2 and PS3 are parts, which can be optionally installed by user's selection, differing from the first pressure sensor PS1 for sensing the intestinal pressure.

Figure 6A:
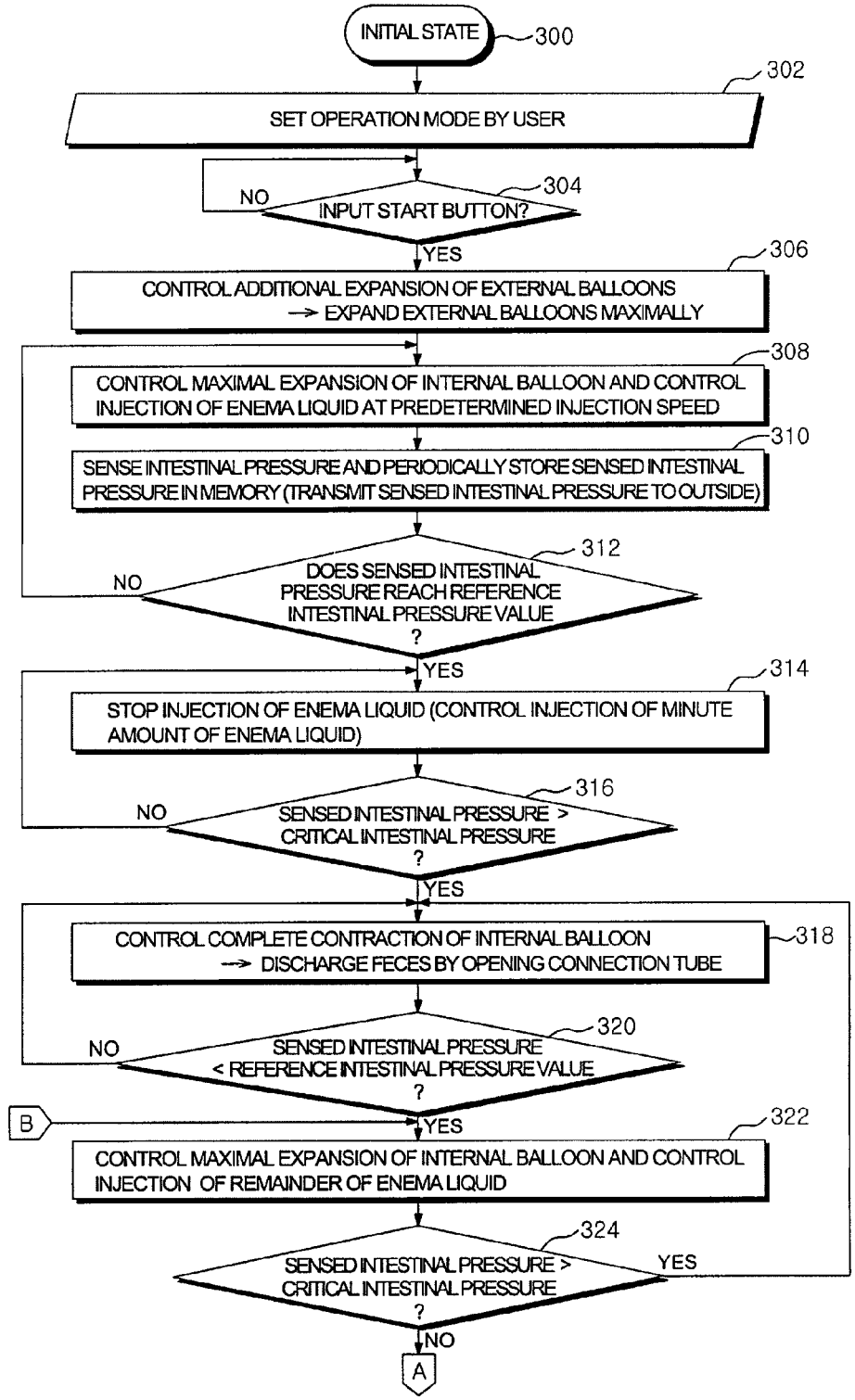
FIGS. 6A to 6C are flow charts illustrating a method for controlling a fecal diverting device in a controlling unit of FIG. 5.
Figure 6B:
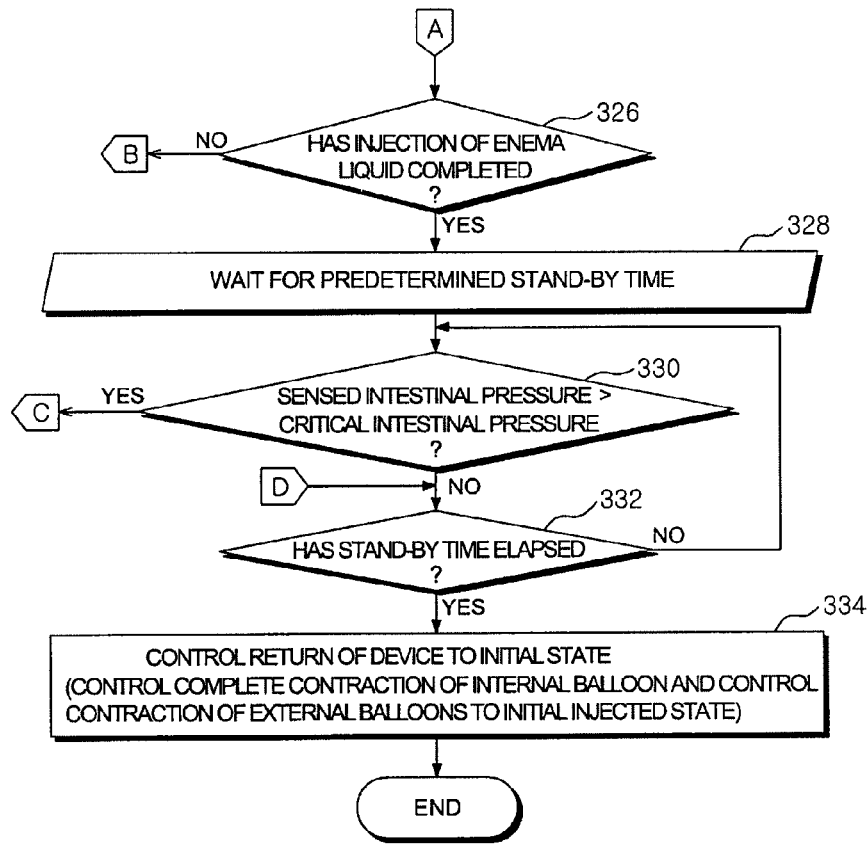
Figure 6C:
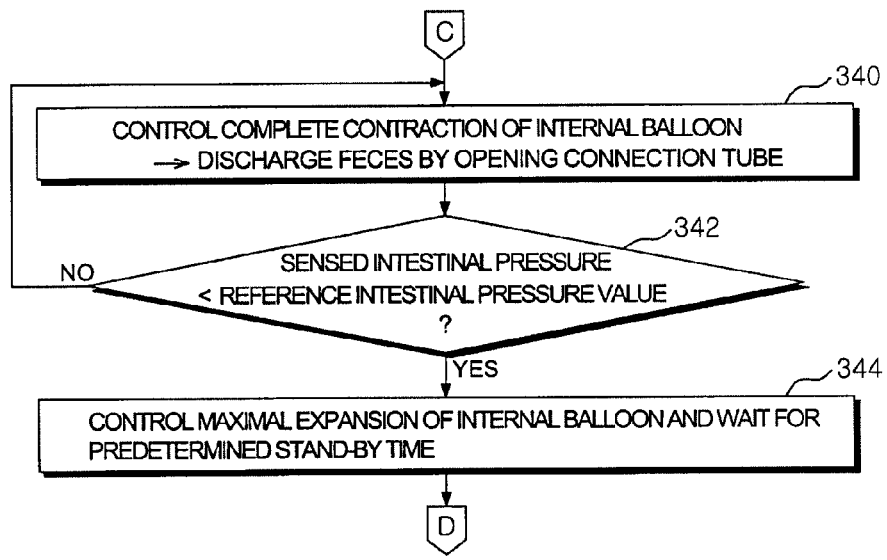

FIGS. 6A to 6C are flow charts illustrating a method for controlling the fecal diverting device 100 in the controlling unit 200 of FIG. 5.

Hereinafter, with reference to the annexed drawings, a fecal diverting operation using the fecal diverting device 100 and the device controller 200 in accordance with an embodiment of the present invention will be described in more detail.

First, an operator inserts the tubular body part 206 of the fecal diverting device 100 into the intestinal tract of a patient above the anastomosed portion 230, and then puts an injector, filled with a filler, into the external balloon connector 12 of the fecal diverting device 100 so that the filler is injected into the external balloon connector 12.

Then, at least two external balloons 208 and 210 are filled with the filler, and thus are expanded. Here, the operator fixes the clamping band 232 to the circumference of the large intestine 226 corresponding to a valley portion 212 between the external balloons 208 and 210, and thus firmly fixes the tubular body part 204 of the connection tube 204 to the inside of the large intestine 226. Further, when the internal balloon 214 is slightly filled with the filler, the operator completely discharges the filler from the internal balloon 214 using an injector connected to the internal balloon connector 10.

Thereby, the connection tube 204 becomes an opened state, and the filling of only the external balloons 208 and 210 is maintained while the internal balloon 214 is not filled with the filler.

The above state refers to a state in which the operation on the large intestine 226 has been completed, and thus becomes an initial state for fecal diversion using the device controller 200 of the present invention.

In the above initial state, the operator removes the respective injectors from the internal balloon connector 10 and the external balloon connector 12 of the control tube 8, respectively inserts the connector 41 of the internal balloon injection tube 40 and the connector 43 of the external balloon injection tube 42 to the internal balloon connector 10 and the external balloon connector 12 of the control tube 8, connects one end of the socket 45 to the enema liquid connector 14 of the control tube 8, and inserts the connector 47 of the enema liquid supply tube 46 to the other end of the socket 45.

In the initial state (in the step 300 of FIG. 6A), the external balloons 208 and 210 are filled with the initial amount of the filler using the injector, and the internal balloon 214 is not filled with the filler, i.e., is completely contracted.

Under the initial state, the operator turns on the device controller 200, and sets a desired operation mode at step 302 using the operating unit 88. Then, the controlling unit 66 stores set values of the operation mode into the memory 90. Set parameters of the operation mode includes an operation frequency per day, an injection amount of the enema liquid, an injection time of the enema liquid, an injection speed of the enema liquid, etc. Preferably, the operation frequency per day is one time to three times, the injection amount of the enema liquid is in the range of 600~1,000 cc, the injection time of the enema liquid is 15 minutes, the injection speed of the enema liquid is 1,000 cc/15 min, and a stand-by time is 30 minutes.

The above-described parameters of the operation mode and set values thereof, and other set values, which will be described later, have been made only for a better understanding of the present invention, and do not limit the scope of the invention. Those skilled in the art will appreciate that various modifications, additions, and substitutions to the specific elements are possible, without departing from the scope and spirit of the invention as disclosed in the accompanying claims.

When the operator presses a start button on the operating unit 88 after the operation mode has been set, the controlling unit 66 determines whether or not the start button is inputted in the step 304 of FIG. 6A, and then performs the next step 306 of FIG. 6A.

As the start button is pressed, the controlling unit 66 controls the second piston operating unit 74 and thus expands the external balloons 208 and 210 maximally, in the step 306 of FIG. 6A. That is, when the controlling unit 66 applies an external balloon control signal OBP, corresponding to additional expansion, to the second piston operating unit 74, the second piston operating unit 74 moves a piston of the second piston pump 76 forwardly to an extent of an additional amount. Thereby, the filler 80b in the second piston pump 76 additionally fills the external balloons 208 and 210 through the external balloon injection tube 42 of the device controller 200 and the control tube 8 of the fecal diverting device 100.

When the external balloons 208 and 210 are expanded maximally, the valley portion between the external balloons 208 and 210, to which the clamping band 232 is fixed, becomes deeper, and thus the tubular body part 206 can be firmly fixed to the inside of the large intestine 226. Accordingly, although the enema liquid 52 is injected into the large intestine 226, it is possible to prevent the tubular body part 206, formed at the front end of the connection tube 204, from being pushed backwardly due to the raised intestinal pressure.

Thereafter, in the step 308 of FIG. 6A, the controlling unit 66 controls the first piston operating unit 70 so as to expand the internal balloon 214 maximally, and simultaneously controls the pumping part 82 so as to inject the enema liquid 52 to the portion of the large intestine 226 above the tubular body part 206 through the enema liquid injection hole 223.

Now, a circuit and mechanical operation of the controlling unit 66 in the step 308 of FIG. 6A will be described in more detail. When the controlling unit 66 applies an internal balloon control signal IBP, corresponding to maximal expansion, to the first piston operating unit 70, the first piston operating unit 70 moves a piston of the first piston pump 72 forwardly to an extent of the maximal expansion of the internal balloon 214. Thereby, the filler 80a in the first piston pump 72 fills the internal balloon 214 through the internal balloon injection tube 40 of the device controller 200 and the control tube 8 of the fecal diverting device 100. For example, the amount of the filler 80a filling the internal balloon 214 is approximately 17~20 cc.

Further, in the step 308 of FIG. 6A, when the controlling unit 66 applies an enema liquid injection control signal PUMP to the pumping part 82, the pumping part 82 pumps the enema liquid 52 stored in the enema liquid supply tub 50. Thereby, the pumped enema liquid 52 is injected into the portion of the large intestine 226 above the tubular body part 206 through the enema liquid supply tube 46, the control tube 8, and the enema liquid injection hole 223. Here, the injection speed of the enema liquid 52 is a value predetermined by the operator or a default value in the operation mode, and, for example, is approximately 1,000 cc/15 min. The amount of the enema liquid 52 to be injected is approximately 600~1,000 cc.

When the injection of the enema liquid 52 into the large intestine 226 is achieved, the controlling unit 66 reads an intestinal pressure sensed by the first pressure sensor PS1, and periodically stores the sensed intestinal pressure in the memory 90 in the step 310 of FIG. 6A. Further, in the case that the controlling unit 66 communicates with an external controlling device, for example, the printer 96 or the PC 94, the controlling unit 66 transmits the sensed intestinal pressure to the external controlling device.

Simultaneously, the controlling unit 66 determines whether or not the sensed intestinal pressure reaches a reference intestinal pressure value, for example, 80 cm $H_2O$ in the step 312 of FIG. 6A. The reference intestinal pressure value means a critical pressure value for stopping the injection of the enema liquid 52.

When the intestinal pressure reaches the reference intestinal pressure value, the controlling unit 66 controls the pumping part 82 so as to stop the injection of the enema liquid 52 in the step 314 of FIG. 6A. However, the controlling unit 66 allows the minute amount of the enema liquid 52 to be continuously injected into the large intestine 226, thus causing the first pressure sensor PS1 to be capable of sensing the intestinal pressure.

Although the injection of the enema liquid 52 at a predetermined injection speed is stopped, the intestinal pressure in the large intestine 226 is gradually increased due to peristalsis, and the first pressure sensor PS1 continuously senses the increase of the intestinal pressure in the large intestine 226.

Thereafter, the controlling unit 66 determines whether or not the sensed intestinal pressure is larger than a predetermined critical intestinal pressure, for example, 120 cm $H_2O$ in the step 316 of FIG. 6A. When it is determined that the sensed intestinal pressure is larger than the critical intestinal pressure, the controlling unit 66 performs the step 318 of FIG. 6A. The critical intestinal pressure is an intestinal pressure value at which the tubular body part 206 formed at the front end of the fecal diverting device 100 can be fixed to the inside of the intestinal tract.

In the step 318 of FIG. 6A, the controlling unit 66 completely contracts the internal balloon 214 so as to completely open the connection tube 204. Thereby, intestinal feces are discharged to the outside of the anus through the connection tube 204 and a discharge hose (not shown), and are collected in the collection pack 9.

Thereafter, the controlling unit 66 determines whether or not the sensed intestinal pressure is smaller than the above reference intestinal pressure value in the step 320 of FIG. 6A. Then, when it is determined that the sensed intestinal pressure is smaller than the above reference intestinal pressure value, the controlling unit 66 performs the step 322 of FIG. 6A. In the step 322 of FIG. 6A, the controlling unit 66 expands the internal balloon 214 maximally so as to close the inlet of the connection tube 204, and simultaneously injects the remainder of the enema liquid 52 into the large intestine 226 through the enema liquid injection hole 223.

Under the above state, the controlling unit 66 continuously senses the intestinal pressure before the injection of the predetermined amount of the enema liquid 52, for example, 1,200 cc, has been completed, and determines whether or not the sensed intestinal pressure is larger than the critical intestinal pressure (120 cm $H_2O$) in the step 324 of FIG. 6A and the step 326 of FIG. 6B. When it is determined that the sensed intestinal pressure is larger than the critical intestinal pressure, the controlling unit 66 performs the steps 322 to 324 of FIG. 6A again, thus allowing the intestinal feces to be discharged to the outside of the anus and then the enema liquid to be injected again into the large intestine 226.

When it is determined that the sensed intestinal pressure is not larger than the critical intestinal pressure and the injection of the enema liquid 52 has been completed in the step 326 of FIG. 6B, the controlling unit 66 perform the step 328 of FIG. 6B. In the step 328 of FIG. 6B, the controlling unit 66 waits for a predetermined stand-by time (for example, approximately 30 minutes). During the above stand-by time, the enema liquid 52 permeates into feces in the large intestine 226, thus diluting the hard state of the feces.

During the above stand-by time, the controlling unit 66 continuously senses the intestinal pressure, ascertains whether the sensed intestinal pressure is greater than a critical intestinal pressure at step 330 and allows the feces to be discharged to the outside of the anus, when the sensed intestinal pressure is larger than the critical intestinal pressure, in the steps 340, 342, 344 of FIG. 6C.

The controlling unit 66 determines whether or not the above stand-by time has elapsed in the step 332 of FIG. 6B. When it is determined that the stand-by time has elapsed, the controlling unit 66 restores the fecal diverting device 100 to its initial state at step 334. That is, the controlling unit 66 completely contracts the internal balloon 214, and slightly contracts the external balloons 208 and 210 to the initial injected state, for example, a state in which the amount of the filler in a liquid phase injected into the external balloons 208 and 210 becomes 35 cc.

Thereby, one cycle of the fecal diversion controlling operation has been finished.

In the case of a patient, which needs to use the fecal diverting device 100 all day long, the operator may set the operation frequency per day to twice to three times. Then, the respective steps of FIGS. 6A to 6C are repeated twice or three times, thus performing the fecal diversion controlling operation.

Preferably, an injector, which manually controls the injection of the remedial liquid, rather than a connector, which controls the injection of the remedial liquid through the device controller 200, is put into the remedial liquid connector 15 located at the other end of the control tube 8 connected to the remedial liquid injection passage 222 of the fecal diverting device 100. Thereby, a patient can spontaneously inject the remedial liquid through the injector.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for diverting feces, comprising:
a tubular body part;
an internal balloon formed at the inside of the tubular body part;
at least one external balloon formed at the outside of the tubular body part;
an enema liquid injection hole formed through a forefront of the tubular body part, so as to allow an enema liquid to be injected into an intestinal tract of a patient through a control tube;
a device controller connected to the control tube so as to control the injection of the enema liquid, supplied from an enema liquid supplying unit, into the intestinal tract through the control tube, the device controller having a memory;
an internal balloon filling unit causing a filler to fill the internal balloon or to be discharged from the internal balloon;
an external balloon filling unit causing the filler to fill the at least one external balloon or to be discharged from the at least one external balloon;
a fecal diverting program in the memory of the device controller for controlling the internal balloon filling unit and the external balloon filling unit; and
an intestinal pressure sensing unit connected to the device controller, the device controller contracting the internal balloon when the intestinal pressure sensing unit senses a pressure greater than a critical pressure to relieve the intestinal pressure without deflating the at least one external balloon.

2. The apparatus according to claim 1, wherein the device controller includes:
the enema liquid supplying unit causing the enema liquid in an enema liquid supply tub to be injected through the control tube and the enema liquid injection hole; and
a controlling unit forming a first interface with a user and controlling the internal balloon filling unit, the external balloon filling unit, and the enema liquid supplying unit using the intestinal pressure sensed by the intestinal pressure sensing unit.

3. The apparatus according to claim 2, wherein the device controller further includes:
an external interface for forming a second interface between the controlling unit and an external controlling device; and
an operating unit for forming the first interface with the user.

4. The apparatus according to any one of claim 2 or 3, further comprising:
a first temperature regulating unit for regulating the temperature of the enema liquid under the control of the controlling unit; and
a second temperature regulating unit for regulating the temperature of the fillers filling the internal balloon and the at least one external balloon under the control of the controlling unit.

5. The apparatus of claim 2, wherein the device controller regulates the amounts of the fillers filling the internal balloon and the at least one external balloon through the control tube based on a predetermined fecal diverting program.

6. The apparatus of claim 1, wherein the device controller contracts the internal balloon after a predetermined amount of time.

7. The apparatus of claim 1, wherein the device controller slightly contracts the at least one external balloon when the internal balloon is deflated.

* * * * *